United States Patent [19]

Haber et al.

[11] Patent Number: 4,619,245
[45] Date of Patent: Oct. 28, 1986

[54] MECHANICAL PROSTHETIC SPHINCTER

[75] Inventors: Terry M. Haber, Lake Forest; William H. Smedley, Mission Viejo, both of Calif.

[73] Assignee: Habley Medical Technology Corporation, Laguna Hills, Calif.

[21] Appl. No.: 522,107

[22] Filed: Aug. 11, 1983

[51] Int. Cl.[4] .............................................. A61B 19/00
[52] U.S. Cl. .................................... 128/1 R; 623/11; 128/DIG. 25
[58] Field of Search ............... 3/1; 128/1 R, DIG. 25, 128/346

[56] References Cited

U.S. PATENT DOCUMENTS

| | | | |
|---|---|---|---|
| 2,455,859 | 12/1948 | Foley | 128/DIG. 25 |
| 3,147,754 | 9/1964 | Koessler | 128/DIG. 25 |
| 3,815,576 | 6/1974 | Balaban | 128/DIG. 25 |
| 4,118,805 | 10/1978 | Reimels | 128/DIG. 25 |

FOREIGN PATENT DOCUMENTS 1174814  12/1969  United Kingdom ....... 128/DIG. 25

Primary Examiner—Richard J. Apley
Assistant Examiner—David J. Isabella
Attorney, Agent, or Firm—Morland C. Fischer

[57] ABSTRACT

The prosthetic sphincter includes a manually controllable actuating component for implantation at a convenient location in a patient's body. This actuating component is mechanically connected through a force applying cable to a responsive component positioned about an elimination passage in the patient such as the distal intestine. The actuating component is in the form of a ring so that manual squeezing of opposite portions causes an elongation of the ring to pull on the cable and thereby open up an occlusion orifice in the responsive component. The actuating component in the form of the ring can upon manual manipulation return to its circular form and thereby permit closing of the occlusion orifice in the responsive component. No batteries or electrical components are required for operating the prosthetic sphincter and no resection of luminal tissue is required for its implementation.

22 Claims, 11 Drawing Figures

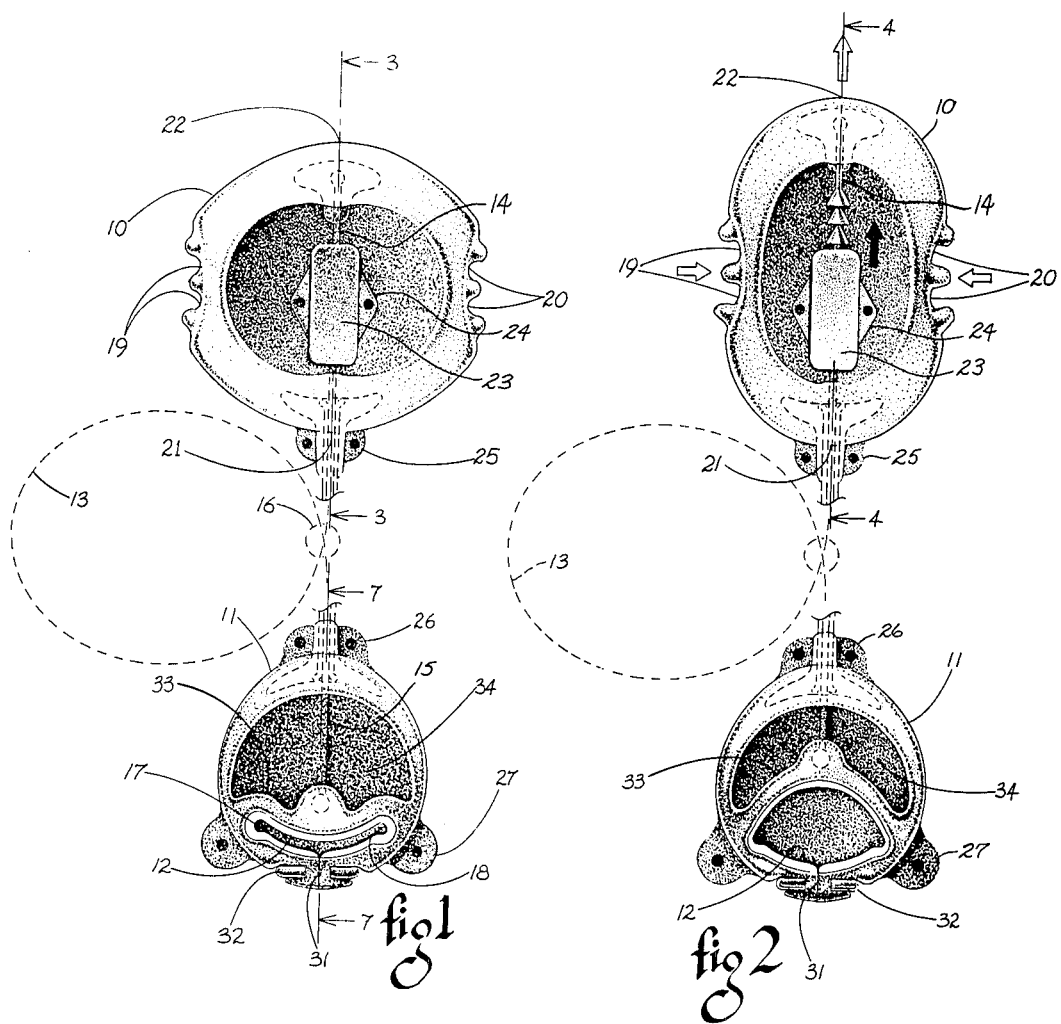
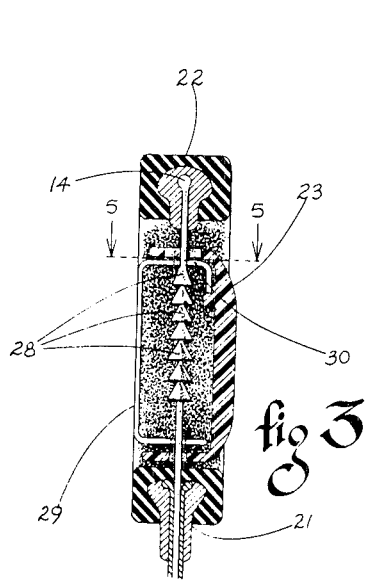

MECHANICAL PROSTHETIC SPHINCTER

FIELD OF THE INVENTION

This invention relates to prosthetic sphincters for implantation in a patient to overcome the problem of incontinence.

BACKGROUND OF THE INVENTION

Conventional colostomies involve a surgical procedure in which the intestine is severed and an end of the intestine is exteriorized through an incision in the abdominal wall of a patient. The anastomosis of the intestine to the peritoneum and skin of the abdominal wall is such as to provide a passage for intestinally-contained fecal matter to pass to the outside of the patient's body. The nipple-like termination of this passage is called the "stoma".

The foregoing operation results in a loss of continence for the patient and he or she must typically wear a polymer pouch on the outside of the body or a reconstructed pouch of surgically enlarged intestinal tissue on the inside of the body in order to collect the fecal matter passing through the abdominal stoma, which additionally necessitates surgical relocation of the intestine from its natural anal opening to an artificial abdominal stoma site. In order to avoid such incontinence, several types of occlusion devices have been proposed for closing off the stoma in order that a patient need not be burdened with a pouch. No such device has had either a true, sphincter-like mechanical action or allowed the intestinal transcutaneous elimination passage to remain in its natural location.

Most such closure devices require a complicated surgical procedure, involving an invasion into the intestine itself. Further, any such closure device located on the abdominal wall or immediately beneath the abdominal wall of the area of the stoma is "unnatural" in its specific location.

Aside from proper control of the distal intestine by closure devices, there is further a need for the use of such devices in controlling other elimination passages such as the urethra for post-prostectomy patients, having undergone the trans-urethral resection procedure.

In my copending patent application Ser. No. 370,099 filed Apr. 20, 1982 and entitled Intestinal Control Valve, now U.S. Pat. No. 4,401,107 there is described an intestinal control valve which can be surgically implanted without invading the intestine itself. Further, the valve can be located at the end of the intestine in a normal or "natural" position of the sphincter muscle. While the valve is designed such that it will close off the distal intestine of a patient in a manner analogous to the operation of a normal sphincter muscle, it requires an electric drive motor incorporated in the valve itself operable from a remote location by appropriate electrical means. As a consequence, the profile is somewhat elongated for this valve. Further, it is necessary to monitor the battery life for supplying electrical power.

In my later filed copending patent application Ser. No. 435,761, there is provided an improved closure device in the form of a synthetic sphincter which again can be readily surgically implanted without ischemia and erosion of the elimination passage. This closure is so designed that there is no need for an electrical drive motor in the closure device itself. Rather a flexible cable is utilized to actuate the same from a remote location. The closure itself can thus be made with a very short axial length or low profile and is thus useful even for smaller diametric elimination passages such as the urethra. Nevertheless, the actuating component for the cable involves the use of a small battery powered electic motor, and thus this device as in my original case has a requirement for periodically monitoring the battery life.

SUMMARY OF THE PRESENT INVENTION

Bearing the foregoing in mind, the present invention contemplates the provision of a greatly improved closure device in the form of a synthetic sphincter which is wholly mechanical in operation. As in my prior patents, this closure can be surgically implanted without invading the particular elimination passage and can also be located at the distal anal-positioned end of the intestine when used to articulate the fecal elimination passage. Further, the present design is such that it will close off the distal colon of the patient in a manner analogous to the operation of the normal sphincter muscle so that maximum comfort to the patient is realizable. The closure also includes a common feature with my more recently referred to copending application in that it exhibits a widely variable profile; that is, its thickness may be increased or decreased in an axial direction and thus is ideally suited for both larger gastrointestinal passages as well as comparably smaller elimination passages such as the urethra.

Briefly, and in its broadest aspect, the mechanical prosthetic sphincter of the present invention includes means defining an occlusion orifice for surrounding the particular elimination passage of the patient to be controlled. Cooperating with the occlusion orifice is means normally biasing the occlusion orifice towards its closed condition, the means being responsive to a manual squeezing force to open the occlusion orifice.

In the preferred embodiment, the means normally biasing the occlusion orifice closed is at a remote location from the means defining the occlusion orifice, and includes a flexible force-applying means responsive to the squeezing force for transmitting force to open the occlusion orifice. Since control is totally manual, no electrical components are necessary. Further, the occlusion orifice is designed with a pressure relief safety feature in the event of no mechanical actuation.

BRIEF DESCRIPTION OF THE DRAWINGS

A better understanding of this invention will be had by now referring to the accompanying drawings in which:

FIG. 1 is a plan view partly schematic in form illustrating the mechanical prosthetic sphincter of this invention in its closed condition;

FIG. 2 is a view similar to FIG. 1 illustrating the components making up the prosthetic sphincter in its open condition;

FIG. 3 is a fragmentary cross section taken in the direction of the arrows 3—3 of FIG. 1;

FIG. 4 is a fragmentary cross section taken in the direction of the arrows 4—4 of FIG. 2;

DETAILED DESCRIPTION OF THE INVENTION

Figure 5:
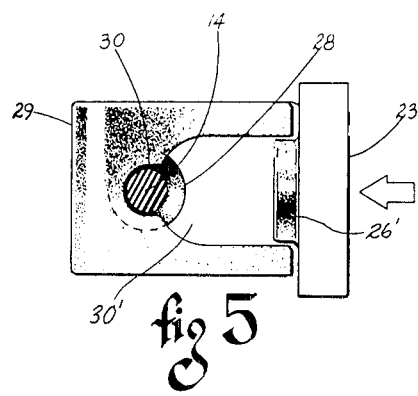
FIG. 5 is a cross section taken in the direction of the arrows 5—5 of FIG. 3.

Referring first to the upper portion of FIG. 1, the prosthetic sphincter includes a manually controllable actuating component 10 cooperating with a responsive component shown in the lower portion of FIG. 1 at 11. The responsive component 11 includes an occlusion orifice 12 shown in closed position but normally arranged to surround the elimination passage of a patient to be controlled by the prosthetic sphincter.

A flexible force-applying cable indicated by the dashed lines 13 has a first end 14 connecting to the actuating component 10 and a second end 15 connected to the responsive component 11. The arrangement is such that a pulling force on the cable will open the occlusion orifice 12.

In FIG. 1, the cable is shown as forming a loop 13 between the actuating component 10 and responsive component 11.

The cross-over point of the loop 13 of the cable is loosely secured by a tie 16 such that the separation distance between the actuating component 10 and responsive component 11 can be varied, this repositioning simply closing down the loop 13 or causing it to become larger. In this manner, insertion at various points in a patient's body of the actuating component and responsive component can more easily be accomplished.

An important feature of the occlusion orifice 12 in the responsive member 11 is that when the same is contracted, it assumes an elongated shallow oval shape as illustrated in FIG. 1, the opposite ends of the oval terminating in purposely formed enlarged openings 17 and 18 to thereby avoid ischemia due to constriction of the arteries surrounding the elimination passage.

Referring once again to the actuating component 10, further details will be evident from FIG. 1. As shown, the same is generally of a ring shape and is provided with indentations 19 and 20 on two diametrically opposite portions of the ring to provide tactile information for guiding a person's fingers to these portions. With the fingers on the portions 19 and 20, manual squeezing of the portions will move them towards each other to cause two other diametrically opposite portions of the ring indicated at 21 and 22, spaced 90° from the indentations 19 and 20, to move away from each other, so that the ring becomes elongated in a vertical direction; that is, assumes an oval shape.

With reference to FIG. 2, the actuating component 10 is shown after it has been squeezed wherein it will be evident that the cable end 14 has been pulled within the ring shape of the component 10. The second end of the cable 15 will thus be pulled upwardly as shown in FIG. 2 to open the occlusion orifice 12 as described briefly heretofore.

It is to be understood that the actuating component ring 10 is resilient and will tend to return to its circular configuration shown in FIG. 1 if squeezing pressure is relieved on the indentations 19 and 20. Similarly, the responsive member 11 and particularly the walls defining the occlusion orifice 12 are biased to return to the closed position illustrated in FIG. 1. Therefore, unless the portion of the cable pulled into the ring as a consequence of the squeezing action is held in its pulled in position, it will simply move in an opposite direction to permit closure of the occlusion orifice 12.

To avoid the foregoing and permit manual control of opening and closing of the occlusion orifice 12, there is provided a releasable retaining means indicated generally by the numeral 23 in FIGS. 1 and 2 for holding the portion of the cable pulled into the ring as a result of squeezing the indentations so that the occlusion orifice 12 is held in its expanded condition automatically until such time as the retaining means 23 is intentionally released.

The retaining means 23 to operate effectively must be stationary with respect to the deformation of the actuating component 10 and towards this end, there are provided integrally formed ears such as indicated at 24 having openings for receiving sutures to secure the same to a patient's body. Similarly, the actuating component 10 includes integrally formed ears such as indicated at 25 so that it can be secured to the patient's body independently of the releasable retaining means 23.

Similar integrally formed suture ears are shown at 26 and 27 by way of example for the responsive component 11.

Referring now to both cross sections of FIGS. 3 and 4, the manner in which the releasable retaining means 23 described briefly in FIGS. 1 and 2 functions will become evident. As shown, the first end 14 of the cable within the actuating component 10 includes a series of serrations indicated at 28. A part of the releasable retaining means, in turn, includes a metal ribbon 29 anchored at its lower end and constituting a spring member defining at its upper end as viewed in FIG. 3 a restricted portion 30 for engaging any one of the serrations juxtaposed thereto. The portion 23 of the releasable retaining means as shown in FIG. 3 when manually depressed or moved to the left as indicated by the arrow in FIG. 4 will function as a manually operable release means for removing the restricted portion 30 from the serration so that the cable end 14 can move in a reverse direction and the ring shape of the actuating component 10 return to its circular configuration.

Figure 6:
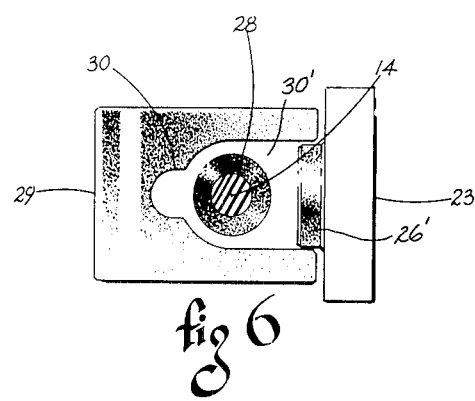
FIG. 6 is a fragmentary cross section taken in the direction of the arrows 6—6 of FIG. 5.

The cross sections of FIGS. 5 and 6 illustrate the foregoing action, wherein FIG. 5 shows one of the serrations 28 trapped within the restricted opening 30 of the spring element or ribbon 29 whereas FIG. 6 illustrates the relative position of the serration 28 when the restricted opening has been removed as by the member 23 being manually urged to the left as viewed in FIG. 6 to move the spring ribbon 29 to a new position 29' indicated in phantom lines in FIG. 4 and in solid lines in FIG. 6. To assure proper indexing of the releasable member 23 with the spring ribbon 29, the restricted opening 30 extends into an enlarged opening 30' engaging opposite sides of an indexing button 23' on the inside of the release 23.

It will be understood that when manual pressure is relieved from the release 23, the ribbon spring 29 will tend to position the restricted opening 30 to its position illustrated in FIG. 5. Because of the conical shape of the individual serrations 28, it will be evident that as the ring shape of the actuating component is squeezed as described in FIGS. 1 and 2, the end 14 of the cable can be pulled upwardly with, the various serrations 28 "clicking" by the restricted opening 30. However, because the opposite or rear ends of the serrations form right angles, when pressure is relaxed they will catch on the restricted opening and prevent reverse movement of the cable until the restricted opening is removed by the member 23 as described.

The responsive component 11 of the prosthetic sphincter described in FIGS. 1 and 2 is specifically designed to control the elimination passage of the distal intestine of a patient and towards this end, the occlusion orifice 12 is of a size so that the same can be positioned about the distal intestine.

With respect to the foregoing and referring once again to the responsive component 11 of FIGS. 1 and 2, it will be noted that this component is of a general ring shape. The bottom portion of this ring includes a division 31 to permit separation of the ring to allow positioning of the occlusion orifice 12 about the elimination passage defined by the distal intestine. A fastener 32 is provided for holding the opposed ring ends defining this division 31 together after the same has been positioned about the elimination passage.

As best shown in FIG. 2, the wall of the occlusion orifice 12 to which the second end is of the cable 13 connects defines a bridging portion 33 extending across the ring to define the occlusion orifice 12 on one side; that is, the lower side as viewed in FIG. 2, and a secondary opening 34 on the other or upper side. It is the portion of the occlusion orifice opposite the bridging portion 33 which constitutes the lower part of the ring shape wherein the division 31 is formed.

Figure 7:
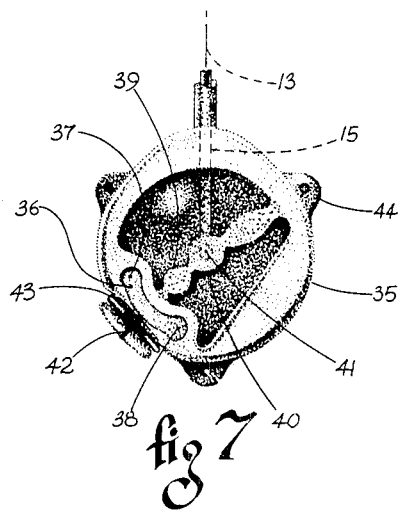
FIG. 7 is a plan view of one of the components of the enclosure particularly useful for closing off the urethra showing the same in its closed position.
Figure 8:
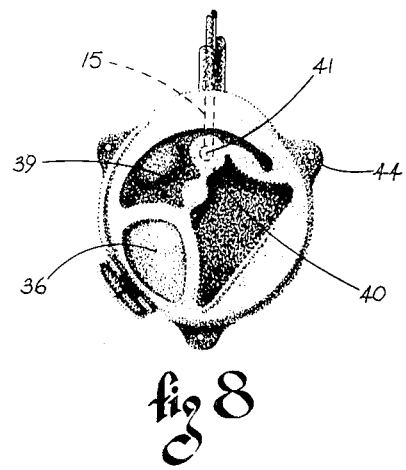
FIG. 8 is a view similar to FIG. 7 but illustrating the component in its open position.

Referring now to FIGS. 7 and 8, there is shown a responsive member 35 designed particularly for surrounding the elimination passage of the urethra of a patient. This responsive member 35 is actuated by a force-applying cable in precisely the same manner as the responsive member 11 described in FIGS. 1 and 2 and in fact, the same second cable end 15 connects to this responsive member 35 as illustrated in FIGS. 7 and 8.

Since the occlusion orifice must be necessarily smaller, some modification of the responsive member is desired and thus the responsive member 35 shown in FIGS. 7 and 8 is somewhat different from that shown in FIGS. 1 and 2. More particularly, the occlusion orifice for the responsive member 35 is shown at 36, this orifice again having opposite ends terminating in enlarged openings 37 and 38 to thereby avoid ischemia of the urethra and urethral arteries as in the embodiment of FIGS. 1 and 2. Also, the one wall of the occlusion orifice 36 defines a first bridging portion 39 extending across the ring to define the occlusion orifice and there is also included a second bridging portion 40 between a mid point of the first bridging portion and a remote portion of the ring. The second end 15 of the cable 13 connects to this second bridging portion at 41 such that a pull opens the occlusion orifice 36 by way of the second bridging portion as most clearly illustrated in FIG. 8.

In the embodiment of FIGS. 7 and 8, the portion of the ring shape defining with the first bridging portion 39 the occlusion orifice 36 is provided with a division 42 permitting separation of the ring to allow positioning of the occlusion orifice 36 about the urethra. A fastener 43 in turn is provided for holding the opposed ring ends defining the division together after the responsive component is in place.

Figure 9:
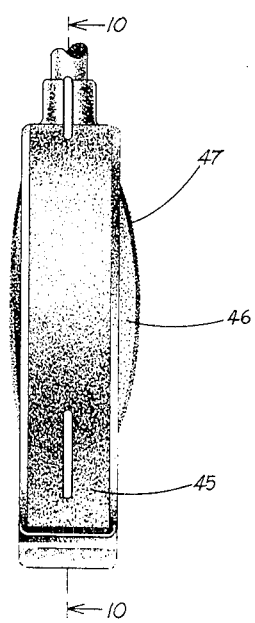
FIG. 9 is a fragmentary side elevational view of a further embodiment of a component of the prosthetic sphincter of this invention.
Figure 10:
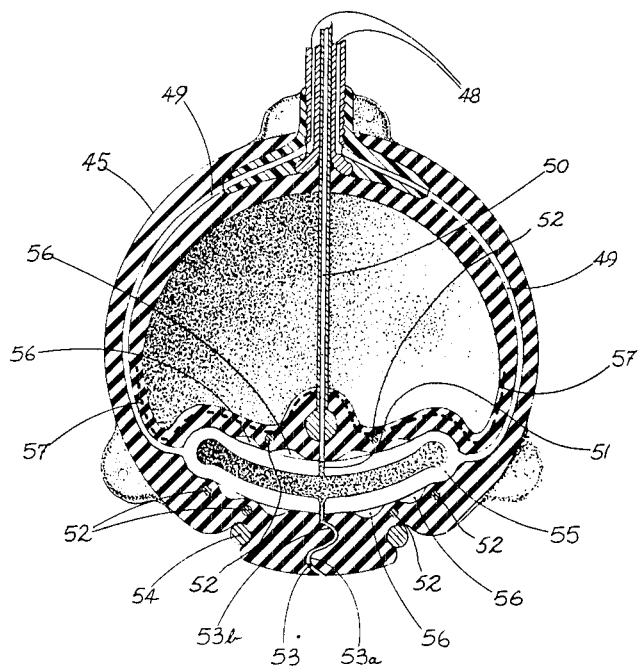
FIG. 10 is a cross section taken in the direction of the arrows 10—10 of FIG. 9.

FIGS. 9 and 10 illustrate in side elevation and front cross section, respectively, a modified responsive component for surrounding an elimination passage operable by the actuating component 10 described in FIGS. 1 and 2. This modified responsive component incorporates further features as will now be described.

Referring first to FIG. 9, the responsive member is indicated at 45 and is filled with a gel lubricant 46 contained by a surrounding tensile skin 47. This gel functions as a hydroelastic dampener during opening and closing of the occlusion orifice.

Referring to the cross section of FIG. 10, it will be understood that the gel and skin will fill the upper opening within the ring shape above the bridging portion defining the top of the occlusion orifice. As shown at the upper portion of FIG. 10, there may be provided fluid delivery passages 48 along the sides of the actuating cable. The responsive member 45 itself is of ring shape as described and includes channels 49 formed in the ring shape extending to the occlusion orifice and communicating with the passages 48. The cable itself may include a central delivery passage 50 connecting through its second end with the occlusion orifice as at 51. The passages 48 and cooperating channels 49 together with the central passage 50 provide a convenient means for introducing appropriate chemicals such as lubricants, anti-irritants and/or drugs to the vicinity of the occlusion orifice and engaging portions with the elimination passage.

The responsive component 45 shown in FIG. 10 is also provided with telemetry responsive means 52 on the bridging portion and ring portion forming the remainder of the occlusion orifice opposite the bridging portion for enabling external detection of the degree of expansion and contraction of the occlusion orifice. As in the case of the other responsive components, the lower end of the ring shape below the occlusion orifice includes a division 53 which includes rounded projections or nubs 53a and 53b for indexing the opposed portions of the ring defining the division in a proper position in alignment in both planes. A fastener 54 if provided to hold the opposed ring portions defining the division 53 together after the occlusion orifice has been positioned about the elimination passage to be controlled.

FIG. 10 also illustrates an occlusion orifice control chamber 55 lining the occlusion orifice and connecting to the channels 59. The inner opposed surfaces of the bridging and ring portion defining the occlusion orifice include passive pressure reduction chambers 56 for relieving pressure on the elimination passage.

Finally, in the embodiment of FIG. 10, there may be provided a tensile resisting mesh 57 passing through the bridging portion and portions of the ring shape at the ends of the bridging portion of the occlusion orifice in a continuous manner as shown.

Figure 11:
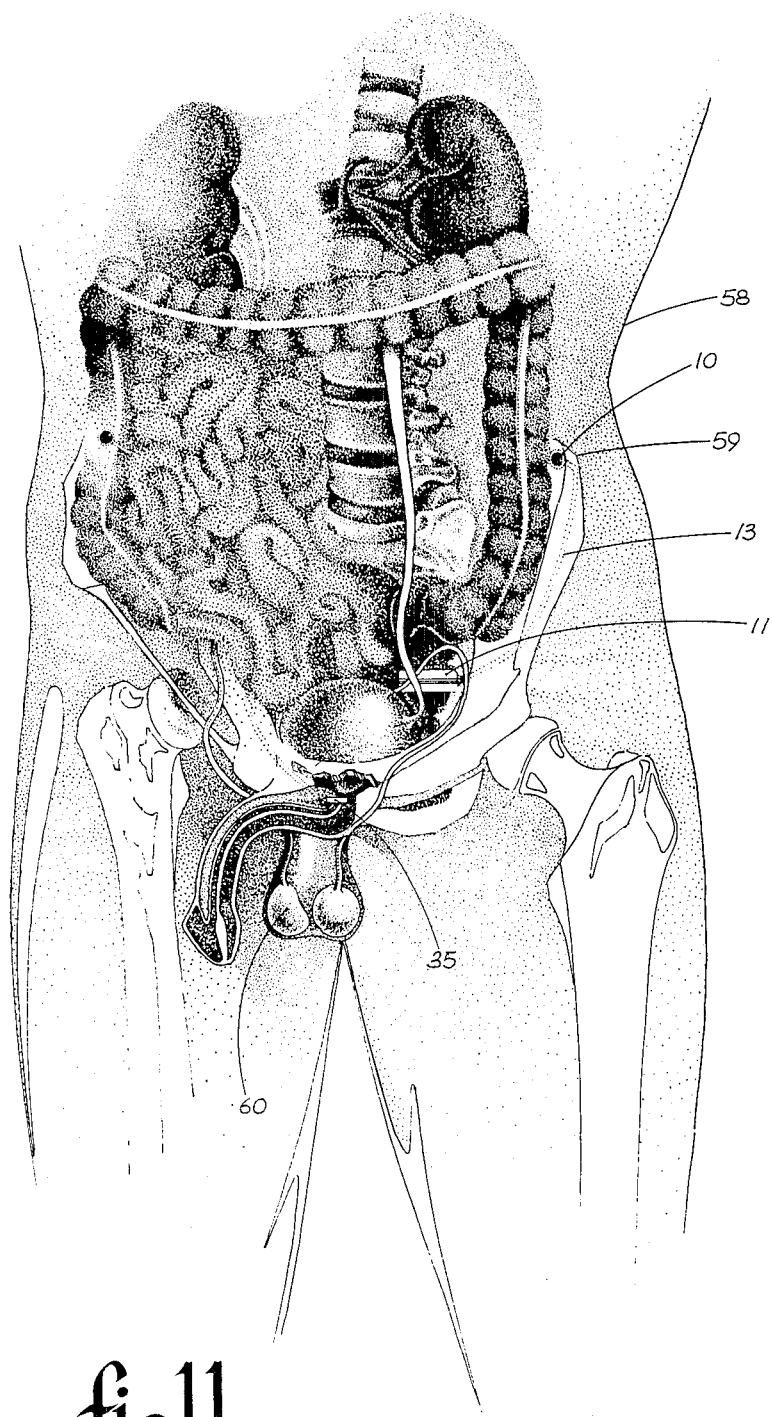
FIG. 11 is a fragmentary broken away view of a patient's lower body portion illustrating various locations for the closure device of the present invention.

Referring now to FIG. 11, there is shown at 58 a patient wherein the actuating component 10 described in FIGS. 1 and 2 is surgically implanted at a specific location at the ilium 59 of the patient. The responsive member 11 in turn is shown surrounding the distal intestine. The cable 13 is indicated in dotted lines extending from the actuating component 10 to the responsive component 11.

Also illustrated in FIG. 11 is the responsive component for the urethra shown in position at 35. An appropriate actuating component may be independently implanted in the scrotum of the patient as indicated at 60. Such actuating component would be the same as the actuating component illustrated at 10 in FIG. 11 although of a reduced size and its implantation in the positon of an excised testicle is merely illustrative of the fact that the actuating component can be located at any convenient site in the patient's body for mechanical actuation.

From all of the foregoing, it will now be evident that the present invention has provided a greatly improved prosthetic sphincter wherein no electrical components are required. Further, it is not necessary to effect any type of resection of the articulated passage. The mechanical action of the actuating component is positive and easy to effect, the various indentations being easily located tactily after implantation in the patient. Further, because of the relative flat profile of the ring shape, the release is readily located on one of the flat surfaces and simple urging of this release will permit closure of the responsive member all as described. The serrations and retaining structure set forth permit any degree of opening and closing to be effected by control of the squeezing. The opening and closing action is appropriately decelerated by the dampening action of the gel.

While the invention has been described with respect to control of elimination passages, it is equally adaptable to intake passages such as the esophagus.

I claim:

1. A mechanical prosthetic sphincter for controlling an elimination passage of a patient for realizing continence, including in combination:
   (a) a manually controllable actuating component in the form of a ring having pressure receiving surfaces on two diametrically opposite portions, the manual squeezing of said pressure receiving surfaces moving said opposite portions towards each other causing two other diametrically opposite portions of said ring to move away from each other such that the ring assumes an oval shape;
   (b) a responsive component having an occlusion orifice for surrounding said elimination passage;
   (c) a flexible force-applying means in the form of a cable having a first end passing through one of said two other portions of the ring and terminating in the other of the two other portions of the ring so that squeezing the pressure receiving surfaces of the ring pulls a portion of the cable into the ring and releasing the pressure receiving surfaces permits said portion to move in an opposite direction, the second end of the cable connecting to a wall of said occlusion orifice in said responsive component such that a pulling force on said second end of said cable expands said occlusion orifice and a movement of the cable in an opposite direction results in a contraction of said orifice; and
   (d) releasable retaining means in said ring for holding the portion of the cable pulled into the ring as a result of squeezing the pressure receiving surfaces so that the occlusion orifice is held in its expanded condition automatically until such time as said retaining means is intentionally released.

2. A mechanical sphincter according to claim 1, in which said occlusion orifice, when contracted, approaches an elongated shallow oval shape, the opposite ends of the oval shape terminating in enlarged openings to thereby avoid ischemia by constriction of adjacent arteries.

3. A mechanical sphincter according to claim 1, in which said actuating component and responsive component include integrally formed ears having openings for receiving sutures to facilitate securing the components in a patient's body.

4. A mechanical sphincter according to claim 1, in which said first end of said cable within said ring includes a series of serrations, said releasable retaining means including a restected portion for engaging any one of the serrations juxtaposed thereto; and manually operable release means on said retaining means for removing said restricted portion from said serration, said ring being biased to assume a circular configuration when no squeezing force is applied thereto.

5. A mechanical sphincter according to claim 1, wherein said responsive member is of a general ring shape, said wall defining a bridging portion extending across the ring to define said occlusion orifice on one side and a secondary opening on the other side, said cable having its second end connected to said bridging portion, said occlusion orifice having a division to permit separation of the ring to allow positioning of the occlusion orifice about said elimination passage; and a fastener for holding the opposed ring ends defining said division together.

6. A mechanical sphincter according to claim 1, wherein said responsive member is of a general ring shape, said wall defining a first bridging portion extending across the ring to define said occlusion orifice and a second bridging portion connected between a mid point of the first bridging portion and a remote portion of the ring, said second end of said cable being connected to said second bridging portion such that a pull on said cable opens said occlusion orifice by way of said second bridging portion, said occlusion orifice having a division to permit separation of the ring to allow positioning of the occlusion orifice about the elimination passage; and a fastener for holding the opposed ring ends defining said division together.

7. A mechanical sphincter according to claim 5, in which said secondary opening of said responsive member is filled with a gel lubricant; and a surrounding tensile containment skin for said gel.

8. A mechanical sphincter according to claim 5, including fluid delivery passages along the sides of said cable, said responsive member having channels formed in the ring shape extending to the occlusion orifice and communicating with said passages, said cable having a central chemical delivery passage connecting through its said second end with said occlusion orifice.

9. A mechanical sphincter according to claim 5, including telemetry responsive means on said bridging portion and the ring portion forming the remainder of said occlusion orifice opposite said bridging portion for enabling external detection of the degree of expansion and contraction of said occlusion orifice.

10. A mechanical sphincter according to claim 8, including an occlusion orifice control chamber lining said occlusion orifice and connecting with said channels.

11. A mechanical sphincter according to claim 10 in which the inner surfaces of the bridging portion and ring portion defining said occlusion orifice include passive pressure reduction chambers for relieving pressure on said elimination passage.

12. A mechanical sphincter according to claim 5, in which said bridging portion and portions of the ring shape at the ends of the bridging portion include a continuous reinforcing lining.

13. A mechanical sphincter according to claim 7, in which said gel has a hydroelastic dampening capability by virtue of the resistance of the gel and encapsulating skin to rapid deformation of their containment chambers.

14. A mechanical prosthetic sphincter for controlling an elimination passage of a patient for realizing continence, said sphincter comprising:
- a responsive component to be implanted at a first location in the patient's body, having an extensible wall defining an occlusion orifice for encircling said elimination passage, said occlusion orifice being normally biased in a closed position;
- a ring-shaped resilient actuating means separate from said responsive component to be implanted at a second location in the patient's body and having at least a first and second oppositely disposed pressure receiving surfaces; and
- a substantially inextensible force applying means connected to and extending between said wall and said actuating means, whereby depression of said oppositely disposed pressure surfaces towards one another causes said ring-shaped actuating means to assume an oval shape thereby displacing said force applying means a distance towards said actuating means and causing a corresponding displacement of said wall thereby opening said occlusion orifice for permitting the movement of material through the patient's elimination passage.

15. The prosthetic sphincter recited in claim 14, wherein said responsive component comprises a hollow body having a flexible bridging portion extending thereacross,
- one side of said bridging portion defining said occlusion orifice, and the opposite side of said bridging portion defining a chamber filled with a force dampening material.

16. The prosthetic sphincter recited in claim 14, further comprising fluid passage means extending through said responsive component for delivering medicinal fluids to said occlusion orifice and to an area of the patient's elimination passage which is surrounded by said occlusion orifice.

17. The prosthetic sphincter recited in claim 14, wherein said force applying means is a flexible cable.

18. The prosthetic sphincter recited in claim 14, further comprising tactile information supplying means formed on each of said pressure receiving surfaces to enable the patient to manually locate and squeeze said pressure receiving surfaces to cause the elongation of said responsive component.

19. The prosthetic sphincter recited in claim 14, further comprising means for releasably retaining a first end of said force applying means at a position within said actuating means when said force applying means is moved away from said responsive component so as to preserve the open condition of said occlusion orifice.

20. The prosthetic sphincter recited in claim 19, wherein said retaining means includes a series of serrations formed along said force applying means and locking means at said actuating means to be moved into engagement with at least one of said serrations to prevent the movement of said force applying means in an opposite direction towards said responsive component.

21. The prosthetic sphincter recited in claim 20, further comprising release means located so as to be manually actuated for moving said locking means out of engagement with said serrations to thereby permit said force applying means to move in a direction towards said responsive component for returning said occlusion orifice to its normally closed condition around the patient's elimination passage.

22. A mechanical prosthetic sphincter for implantion in the body of an incontinent patient to control the movement of material through an elimination passage of the patient, said sphincter comprising:
- a responsive component to be implanted at a first location in the patient's body, having an extensible wall defining an occlusion orifice for encircling said elimination passage, said occlusion orifice being normally biased in a closed position;
- a resilient actuating means to be implanted at a second location in the patient's body having at least a first and second oppositely disposed pressure receiving surfaces; and
- a substantially inextensible cable means connected to and extending between said wall and said actuating means, whereby depression of said first and second pressure receiving surfaces in a horizontal plane towards each other causes said actuating means to elongate in a vertical plane thereby displacing the cable means a distance toward said actuating means and causing a corresponding displacement of said wall thereby opening said occlusion orifice for permitting the movement of material through the patient's elimination passage.

* * * * *